(12) United States Patent
Lampropoulos et al.

(10) Patent No.: US 7,547,296 B2
(45) Date of Patent: Jun. 16, 2009

(54) SELF SUTURING ANCHOR DEVICE

(75) Inventors: Fred P. Lampropoulos, Salt Lake City, UT (US); Arlin Dale Nelson, Sandy, UT (US); Brian Stevens, Pleasant Grove, UT (US); Greg McArthur, Sandy, UT (US); William Padilla, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 193 days.

(21) Appl. No.: 11/535,454

(22) Filed: Sep. 26, 2006

(65) Prior Publication Data

US 2007/0066942 A1 Mar. 22, 2007

Related U.S. Application Data

(63) Continuation-in-part of application No. 11/202,484, filed on Aug. 11, 2005, which is a continuation-in-part of application No. 11/198,666, filed on Aug. 5, 2005, which is a continuation-in-part of application No. 11/082,170, filed on Mar. 16, 2005.

(60) Provisional application No. 60/627,485, filed on Nov. 12, 2004, provisional application No. 60/623,502, filed on Oct. 29, 2004.

(51) Int. Cl.
*A61M 5/32* (2006.01)

(52) U.S. Cl. .................................... 604/180

(58) Field of Classification Search ............. 604/116, 604/117, 174–180; 606/139–153
See application file for complete search history.

(56) References Cited

U.S. PATENT DOCUMENTS

| | | | |
|---|---|---|---|
| 2,669,231 A * | 2/1954 | Fisher | 604/179 |
| 4,372,073 A | 2/1983 | Goldman | |
| 4,869,719 A | 9/1989 | Hogan | |
| 4,874,380 A | 10/1989 | Hesketh | |
| 5,224,935 A * | 7/1993 | Hollands | 604/180 |
| 5,416,952 A * | 5/1995 | Dodge | 24/68 R |
| 5,911,229 A | 6/1999 | Chodorow | |
| 6,138,866 A * | 10/2000 | Lambelet et al. | 221/25 |
| 6,554,297 B2 | 4/2003 | Phillips et al. | |
| 2001/0037119 A1 | 11/2001 | Schmieding | |
| 2002/0072713 A1* | 6/2002 | Almond et al. | 604/167.05 |
| 2006/0095008 A1 | 5/2006 | Lampropoulos et al. | |
| 2006/0095009 A1 | 5/2006 | Lampropoulos et al. | |

OTHER PUBLICATIONS

European Search Report, PCT/US2005/038910 dated Aug. 20, 2007, 8 pages.

(Continued)

*Primary Examiner*—Nicholas D Lucchesi
*Assistant Examiner*—Nathan R Price
(74) *Attorney, Agent, or Firm*—Ryan D. Benson; Stoel Rives, LLP

(57) ABSTRACT

A catheter securement device which automatically deploys one or more sutures to secure a catheter without requiring the practitioner to manually suture the catheter to the self-suturing anchor device. A ratchet mechanism having one or more rotatable ratchet members, which pivot, and a ratchet member engagement spring, which maintains contact between the teeth of the rotatable ratchet member and the teeth of the ratchet ring. A suture retention assembly is provided to maintain the position of the sutures to minimize disruption of the sutures before deployment of the sutures.

10 Claims, 12 Drawing Sheets

OTHER PUBLICATIONS

International Search Report and Written Opinion—Apr. 10, 2008.
International Search Report and Written Opinion—Jun. 14, 2006.

US Office Action for 11/202,484 dated Jul. 29, 2008.
US Office Action for 11/532,056 dated Jul. 29, 2008.

* cited by examiner

SELF SUTURING ANCHOR DEVICE

CROSS REFERENCE TO RELATED APPLICATIONS

This application is a continuation-in-part application to U.S. Nonprovisional patent application Ser. No. 11/202,484, filed on Aug. 11, 2005, entitled, "Self Suturing Anchor Device," which claims the benefit of priority as a continuation-in-part to U.S. Nonprovisional patent application Ser. No. 11/198,666, filed on Aug. 5, 2005, entitled "Self-suturing Anchor Device for a Catheter," which claims the benefit of priority as a continuation-in-part to U.S. Nonprovisional patent application Ser. No. 11/082,170, filed on Mar. 16, 2005, entitled "Self-suturing Anchor Device for a Catheter," which claims the benefit of priority to U.S. Provisional Patent Application Ser. No. 60/627,485, filed on Nov. 12, 2004, entitled "Self Suturing Anchor Device for a Catheter" and U.S. Provisional Patent Application Ser. No. 60/623,502, filed on Oct. 29, 2004, entitled "Self Suturing Anchor Device for a Catheter," for which the entire specifications of all of the aforementioned applications are incorporated herein by reference.

BACKGROUND

1. The Field of the Invention

Exemplary embodiments relate to the field of catheters, and, more particularly, to a self-suturing anchor device for use with a catheter.

2. Background and Relevant Art

Catheters play an important role in the treatment and care of patients in modern medicine. In particular, catheters provide relatively unobtrusive access to remote portions of a patient's body, allowing desired procedures or treatments to be performed.

A wide variety of generalized and specialized catheters have been developed and refined for particular uses. For example, angioplasty catheters have been adapted to provide a safe and effective conduit for the delivery of a stent and/or balloon to a narrowing or loading blockage in a patient's artery or vein. Drainage catheters are configured to be inserted into a cavity surrounding a patient's kidney, liver or other organ to drain excess fluid or infection from the cavity.

In addition, a number of devices and implements have been developed for use with catheters, to facilitate their effectiveness, or to overcome inherent difficulties associated with their use. For example, catheters that are designed to remain placed in a patient for long periods of time, such as for ongoing care or treatment of the patient, present a number of difficulties. Such catheters must be secured to the patient in a manner that minimizes movement of the catheter that could harm the patient, or otherwise interrupt proper functioning of the catheter.

Accordingly, one approach in the prior art has been to suture the catheter directly to the patient's skin. However, when a patient repositions himself/herself in bed, the catheter may pull at the suture site or bend the catheter. Another approach is to inflate a balloon associated with the distal end of the catheter inside the patient. However, at times an incoherent patient may attempt to withdraw or otherwise remove the catheter. This can cause injury to the catheter insertion site, or can interfere with proper operation of the catheter.

In view of these and other problems in the art, a number of devices have been developed to secure a catheter in a manner that minimizes movement of the catheter, or minimizes interference with its proper operation. Typically, such devices include an adhesive layer to be secured to the patient with a small bore for accommodating the catheter and an adhesive strip to secure the catheter relative to the adhesive layer. Devices such as these are useful because they can be employed by a practitioner to maintain the desired positioning of the catheter. Such devices, however, can be undesirable due at least in part to the fact that they typically cover or otherwise obstruct the catheter insertion site. This can make it difficult to identify infections, drainage, or other complications that may occur at the catheter insertion site. Furthermore, the devices can also obstruct cleaning of the insertion site, such that the site can only be cleaned by removing the anchor devices. Additionally, conventional anchor devices typically utilize a clip, or other securement member which typically is rigid or has a high profile when utilized to secure the catheter. As a result, the securement device can be uncomfortable if pressed against the patient by a chair, bed, or other object.

BRIEF SUMMARY OF SOME EXAMPLE EMBODIMENTS

Catheter securement devices are disclosed herein. According to some examples discussed herein, catheter securement devices are provided which automatically secure the catheter without requiring the practitioner to manually suture the catheter to the self-suturing anchor device. The self-suturing anchor device has a securement mechanism which is adapted to be actuated by the user to automatically secure the catheter in a quick and efficient manner.

In one embodiment, a rotatable ring is provided in connection with the self-suturing anchor device to automatically secure the catheter. At least one suture thread extends from the rotatable ring. When a user pulls the suture in a rearward direction, a loop portion of the suture is freed from the rotatable ring and initially engages a portion of the catheter associated with the bottom of the rotatable ring. The user can then rotate the rotatable ring in one or both of a clock-wise or a counter clock-wise direction to deploy one or more additional suture. Rotation of the rotatable ring tensions the additional suture to automatically secure the portion of the catheter positioned centrally within the rotatable ring. Once the additional suture has been secured, the first suture can be further tightened and tied to further secure the catheter.

The rotatable ring is utilized in connection with a ratchet mechanism. The ratchet mechanism allows movement of the rotatable ring in a first direction while preventing movement of the rotatable ring in the opposite direction. As a result, the rotational position of the rotatable ring is secured against movement. When the user rotates the rotatable ring to deploy, secure, and/or tighten the sutures relative to the catheter, movement of the rotatable ring does not result in loosening of the sutures. Additionally, where the tension on the sutures decreases due to factors such as the natural loosening of the fibers of the suture, the user can easily ratchet the rotatable ring an additional amount to return the sutures to a desired degree of tensioning.

The ratchet mechanism includes ratchet members, such as rotatable ratchet members. The rotatable ratchet members pivot or flex, allowing for movement of the portion of the rotatable ratchet member having teeth. Additionally, in one example a ratchet member engagement spring is provided which maintains contact between the teeth of the rotatable ratchet member and the teeth of the ratchet ring. The ratchet member engagement spring can flex or undergo other deformation to allow for sliding of the teeth of the rotatable ratchet member over the teeth of the ratchet ring during rotation of the rotatable ring.

In one embodiment, a suture retention assembly is provided to maintain the position of the sutures beneath the rotatable ring. The suture retention assembly includes a retention element, such as a flat washer and a bias element, such as a wave spring. The suture retention assembly is configured to be positioned between the rotatable ring and the base. Maintaining the position of the sutures minimizes disruption of the sutures before deployment.

Additional possible aspects of some exemplary anchor devices will be set forth in the description which follows. These and other possible aspects will become more fully apparent from the following description and appended claims.

BRIEF DESCRIPTION OF THE DRAWINGS

In order to describe the manner in which the above-recited and other aspects can be obtained, a more particular description of some examples briefly described above will be rendered by reference to specific embodiments thereof which are illustrated in the appended drawings. Understanding that these drawings depict only some embodiments and are not therefore to be considered to be limiting of its scope, anchor devices will be described and explained with additional specificity and detail through the use of the accompanying drawings in which.

DETAILED DESCRIPTION OF SOME EXAMPLE EMBODIMENTS

Figure 1:
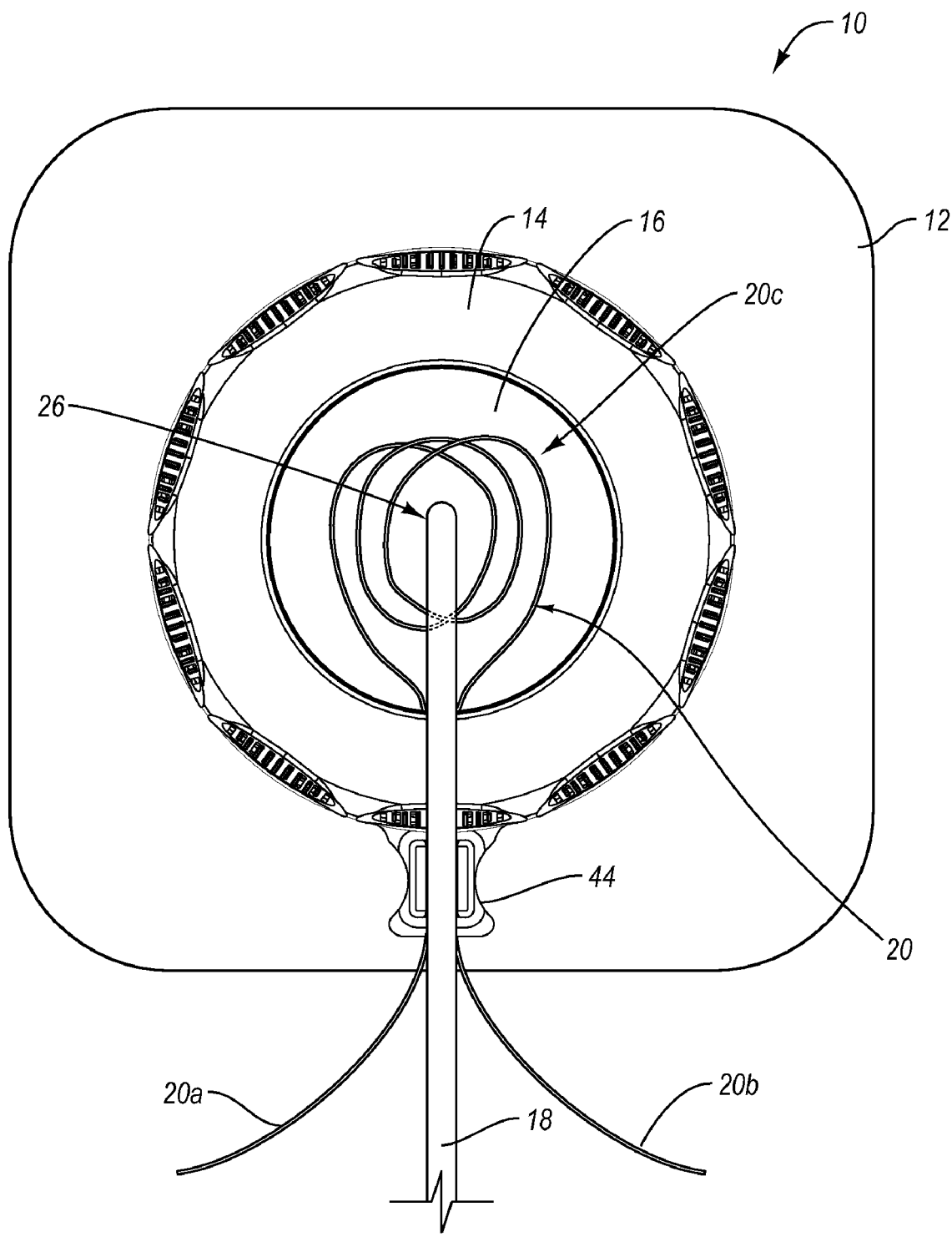
FIG. 1 is a top view of the catheter anchor device illustrating deployment of a first suture according to one example.

Catheter securement devices are disclosed herein. According to some examples disclosed herein catheter securement devices are provided which automatically secure the catheter without requiring the practitioner to manually suture the catheter to the self-suturing anchor device. The self-suturing anchor device has a securement mechanism, which is adapted to be actuated by the user to automatically secure the catheter in a quick and efficient manner.

According to at least one example disclosed herein, the rotatable ring is used in connection with a ratchet mechanism. The ratchet mechanism allows movement of the rotatable ring in a first direction while controlling movement of the rotatable ring in the opposite direction. As a result, the rotational position of the rotatable ring is secured. The ratchet mechanism includes ratchet members. The ratchet members pivot and/or flex to allow for slight movement of the portion of the rotatable ratchet member having the teeth. Additionally, in one example a ratchet member engagement spring is provided which maintains contact between the teeth of the rotatable ratchet member and the teeth of the ratchet ring. The ratchet member engagement spring can flex or undergo other deformation to allow for sliding of the teeth of the rotatable ratchet member over the teeth of the ratchet ring during rotation of the rotatable ring.

In one embodiment, a suture retention assembly is provided to maintain the position of the sutures beneath the rotatable ring before the sutures are deployed. According to one example, the suture retention assembly includes a retention element, such as a flat washer and a bias element, such as a wave spring. The retention element and bias element are configured to be positioned between the rotatable outer ring and the base. In particular, in the case of a flat washer and a wave spring, the flat washer may be positioned against the base while the wave spring is positioned against the rotatable outer ring. In such a configuration, the wave spring urges the flat washer into contact with the base to maintain the sutures positioned within the base. More specifically, according to one example, the base includes a suture storage channel formed therein. The wave spring urges the flat washer into contact with the top of the suture storage channel to maintain the position of the sutures within the suture storage channel. Maintaining the position of the sutures in this way minimizes disruption of the sutures before deployment.

According to one embodiment, a method of assembling the catheter anchor device is provided. Loading of the sutures is facilitated by mounting the base of the anchor device on a loading block. A suture loading cylinder is positioned through the center bore of the catheter anchor device and the center aperture. The suture loading cylinder is utilized to provide a quick and effective mechanism for forming the loop configurations and for loading the sutures in the base.

According to another embodiment of the present invention, one or more components of the catheter anchor device are snapped together or otherwise pressed together to facilitate assembly of the catheter anchor device. For example, multiple pins of the rotatable outer ring are configured to be snapped to securement bores of the bearing members. A plurality of access bores may also be provided in connection with the base of the anchor device such that a staking tool can be inserted through the access bores of the catheter anchor device to flare the pins of the rotatable outer ring to the securement bores of the bearing member.

FIG. 1 is a top view of an anchor device 10 according to one example. Anchor device 10 is utilized to secure a catheter relative to a patient while allowing access to a catheter insertion site for observation and care of the catheter insertion site. Anchor device 10 provides a simple and effective mechanism for securing a catheter by automatically deploying one or more sutures to secure the catheter. In the illustrated embodiment, anchor device 10 comprises an adhesive sheet 12, rotatable ring 14, and a center aperture 16. A catheter 18 is shown being utilized in connection with anchor device 10. Catheter 18 has been inserted into the patient at a catheter insertion site 26.

Anchor device 10 has been placed over catheter 18 such that catheter 18 is threaded through the middle of center aperture 16. Catheter insertion site 26 is positioned approximately in the middle of center aperture 16 such that rotatable ring 14 is positioned and centered about catheter insertion site 26. Adhesive sheet 12 has an adhesive backing which securely fastens anchor device 10 to the patient's skin before and after deployment of the sutures of anchor device 10. Rotatable ring 14 is utilized to automatically deploy one or more sutures for securement of catheter 18.

Center aperture 16 is configured to allow access to catheter 18 at the catheter insertion site 26. By providing access to catheter insertion site 26, a practitioner can observe the condition of the catheter insertion site 26 and provide treatment and care of the catheter insertion site 26 as needed. This can be important in the event of injury, infection, drainage, or other disruptions of catheter insertion site 26. The ability to care for catheter insertion site 26 can be quiet helpful, particularly where catheter 18 is utilized in a gastric or similar setting where regular care and treatment of the catheter insertion site 26 is necessary to maintain the health of the patient and proper operation of catheter 18.

In the illustrated embodiment, a first suture 20, which is utilized to secure catheter 18, is shown being partially deployed. First suture 20 comprises a first end 20a, a second end 20b, and a loop portion 20c. A user grasps first end 20a and second end 20b. The user then retracts first end 20a and second end 20b in a rearward fashion to draw the loop portion 20c of the first suture 20 from under the rotatable ring 14 and to partially deploy the loops of the loop portion 20c of first suture 20. In the illustrated embodiment, the loop portion 20c of first suture 20 is a double loop forming a clove hitch-type securement knot. A second suture 21 (FIG. 2) may then be deployed. The second suture 21 is deployed by rotating rotatable ring 14. In one example, preliminarily freeing the loop portion 20c of the first suture 20 allows the rotatable ring 14 to be rotated with less torque, thereby facilitating deployment of the second suture 21. Additionally, initially freeing the first suture 20 before actuating rotatable ring 14 may also reduce the likelihood that the first suture 20 and the second suture 21 will become tangled as the second suture 21 is deployed. After the second suture 21 is fully deployed and securely fastened about catheter 18, first end 20a and second end 20b can retracted to secure the loop portion 20c adjacent the bottom of rotatable ring 14. Next, the ends 20a, b may then be tied about the portion of catheter 18 adjacent the extension saddle 44. This provides two different points of securement of catheter 18 by the first suture 20 relative to anchor device 10. By providing two points of securement, first suture 20 minimizes twisting and/or pulling of catheter 18 that could result in injury of the patient tissue at catheter insertion site 26.

In addition to minimizing twisting and/or pulling of the catheter 18, the anchor device 10 may be configured to minimize discomfort of the anchor device 10 when the patient moves or bends. For example, according to one embodiment, the adhesive sheet 12 extends a sufficient distance beyond the extension saddle 44 to provide cushioning or protection for the patient with respect to the extension saddle 44.

As will be appreciated by those skilled in the art, a variety of types and configurations of anchor devices can be utilized without departing from the scope and spirit of the present invention. For example, in one embodiment, only a first suture is utilized to secure the catheter. In another embodiment, the suture is comprised of braided nylon, monofilament material, woven silk thread, or other known or conventional string, wire, and/or other suture materials.

Figure 2:
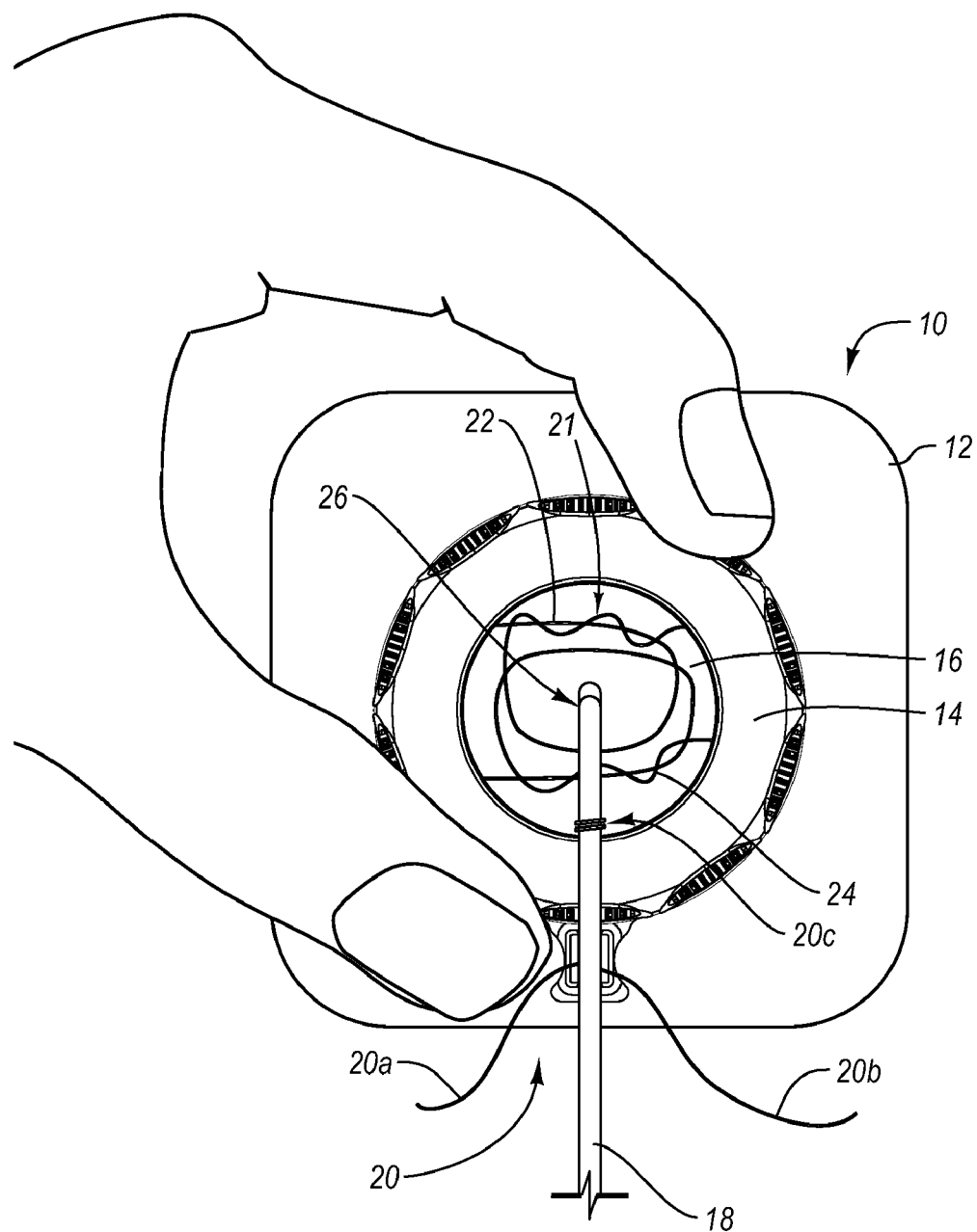
FIG. 2 is a top view of the catheter anchor device illustrating deployment of a second suture relative to the catheter according to one example.

FIG. 2 is a top view of anchor device 10 illustrating a user actuating rotatable ring 14 of anchor device 10, according to one embodiment. In the illustrated embodiment, anchor device 10 includes a second suture 21 with a first portion 22 and a second portion 24, which are housed beneath rotatable ring 14 prior to actuation of rotatable ring 14. In particular, FIG. 4 illustrates the first suture 20 in position beneath a retention element 202. Deploying the first suture 20 frees the first suture 20 from beneath the retention element 202. Once the loop portion (20c, FIG. 2) of first suture 20 is freed from the suture storage channel 40, a user begins to rotate rotatable ring 14 to deploy second suture 21. As the user rotates rotatable ring 14, the second suture 21 automatically deploys and begins to loop about the portion of catheter 18 adjacent catheter insertion site 26. Returning to the embodiment illustrated in FIG. 2, the ends of first portion 22 and second portion 24 of the second suture 21 are actuated from opposite sides of rotatable ring 14 such that both first portion 22 and second portion 24 anchor catheter 18 from opposite sides of the catheter insertion site 26. As a result, two lateral securement positions are provided on each side of catheter 18 to minimize movement of catheter 18 at catheter insertion site 26. Securement of catheter 18 at catheter insertion site 26 will be discussed in more detail with respect to FIG. 3. The loops of first portion 22 and second portion 24 are formed using a double or triple knot configuration to provide a slip resistant knot when secured to catheter 18.

As will be appreciated by those skilled in the art, a variety of types and configurations of anchor device 10 can be utilized without departing from the scope and spirit of the present invention. For example, multiple sutures can be provided in connection with deployment of the rotatable ring rather than a single suture. In another embodiment, more than two sutures are provided in connection with actuation of rotatable ring 14. In yet another embodiment, a plurality of rotatable rings are provided with each rotatable ring deploying one or more sutures to secure catheter 18 in subsequent steps of actuation during use of the anchor device.

Figure 3:
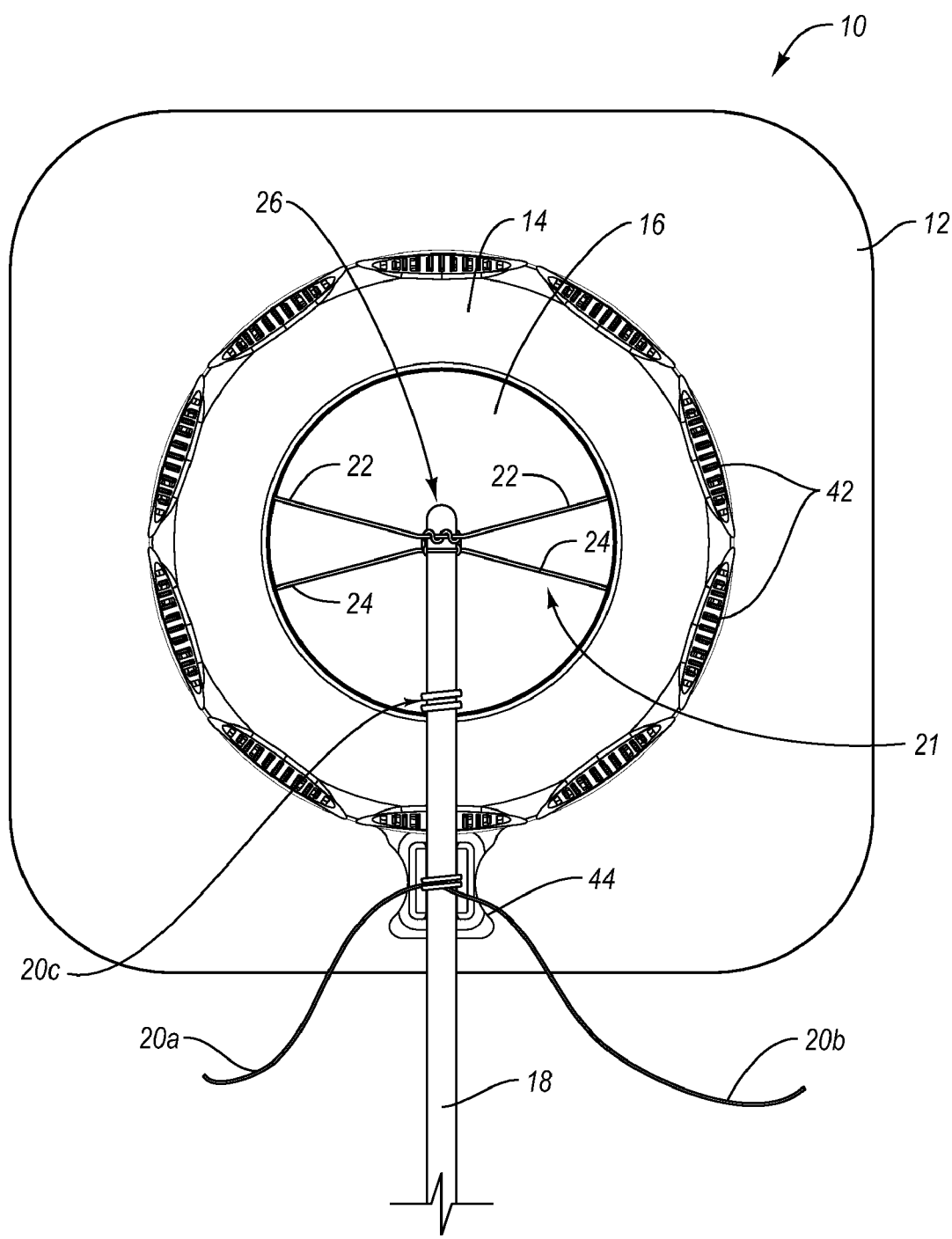
FIG. 3 is a top view of a catheter anchor device illustrating securement of the catheter subsequent to deployment of the sutures according to one example.
Figure 4:
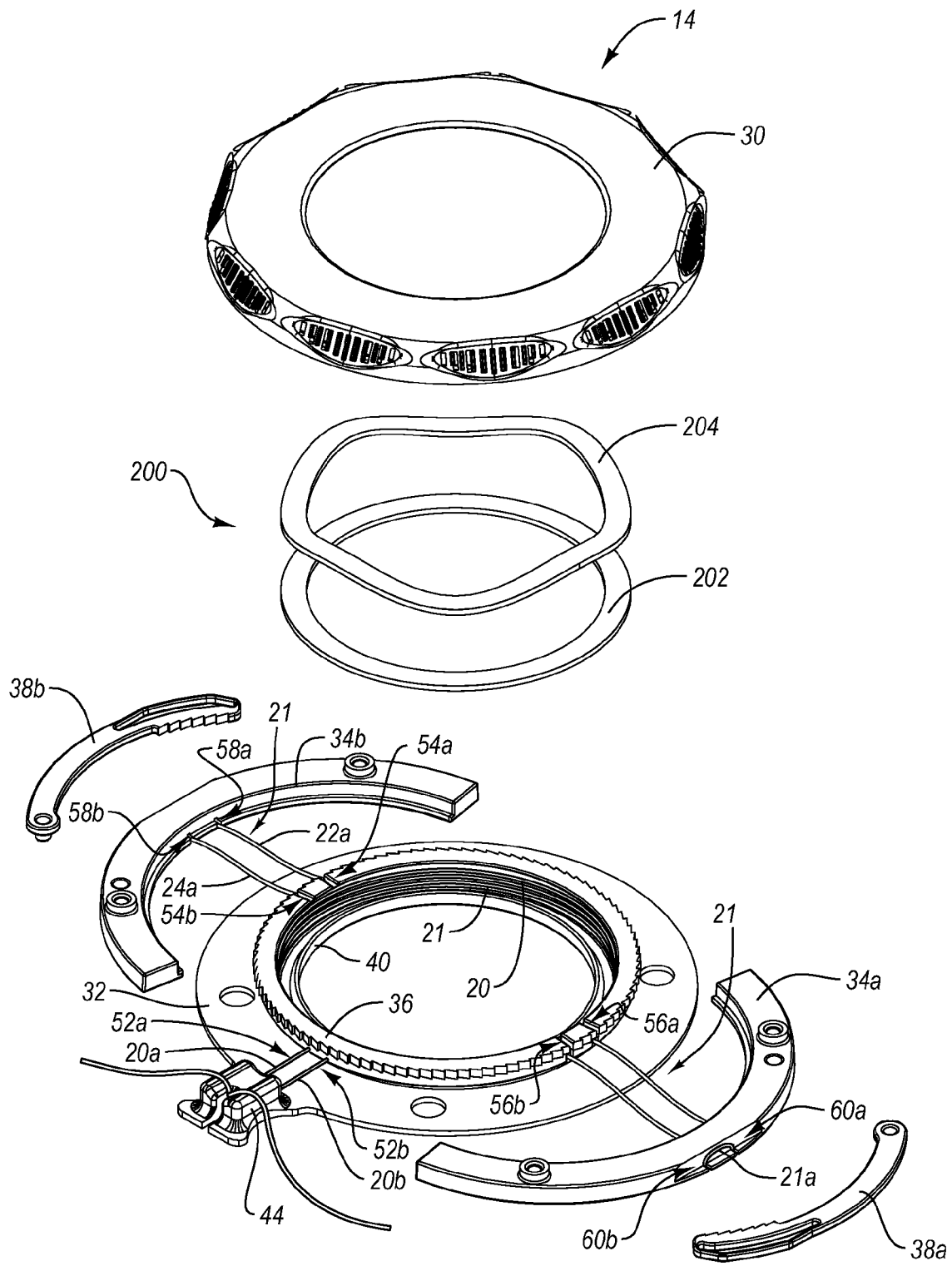
FIG. 4 is an exploded view of the catheter anchor device illustrating the components of the catheter anchor device including a suture retention assembly and rotatable ratchet members according to one example.

FIG. 3 is a top view of anchor device 10 subsequent to actuation of rotatable ring 14 and securement of first suture 20. In the illustrated embodiment, catheter 18 is secured by the first and second portions 22, 24 of the second suture 21, subsequent to actuation of rotatable ring 14. Once second suture 21 has been deployed, the first suture 20 may be further secured by retracting the ends 20a, b of the first suture 20 to tighten loop portion 20c. The first and second ends 20a, b of first suture 20 are then tied adjacent extension saddle 44. Extension saddle 44 provides a desired degree of displacement between the points of securement provided by suture 20 relative to catheter 18. The displacement provided between the points of securement of first suture 20 is sufficient to substantially minimize kinking, twisting, or other manipulation of catheter 18 that could result in damage to the patient tissue at catheter insertion site 26 resulting from movement of catheter 18. Additionally, extension saddle 44 provides a groove which accommodates catheter 18 to minimize kinking, pinching, or other pressure on catheter 18 from the transition over the top of rotatable ring 14.

The portion of catheter 18 positioned adjacent catheter insertion site 26 is secured by the first and second portions 22, 24 of the second suture 21. A part of the first portion 22 is positioned on the left side of rotatable ring 14, while another part of the first portion 22 is secured adjacent the right side of rotatable ring 14. One part of second portion 24 is secured adjacent the left side of rotatable ring 14, while another part of second portion 24 is secured adjacent the right side of rotatable ring 14. As a result, a total of four separate points of securement are provided at the portion of catheter 18 adjacent catheter insertion site 26 to minimize both lateral and forward and rearward movement of catheter 18 during usage of catheter anchor device 10. This provides a safe and reliable securement of catheter 18 during usage while also providing access to the catheter insertion site 26 for cleaning and care of the catheter and/or patient tissue at the catheter insertion site 26. In the illustrated embodiment, a plurality of scallops 42 is shown on rotatable ring 14. Scallops 42 facilitate gripping of rotatable ring during actuation of rotatable ring as shown in FIG. 2. Scallops 42 comprise a concave depression in the outward surface of rotatable ring 14. By providing a concave depression in the outward surface of rotatable ring 14, scallops 42 provide gripping members which minimize any potential abrasion to the patient or practitioner utilizing anchor device 10.

The configuration of anchor device 10 and rotatable ring 14 allow for quick, simple, and effective securement of catheter 18 subsequent to placement of catheter 18 in a patient. This not only shortens the length of the catheter securement procedure and, thus, the entire catheter placement procedure, but also is sufficiently simple such that an assisting nurse or other caretaker can secure catheter 18 while the physician attends to other aspects of the procedure being performed. This is not only more efficient from the standpoint of operating room economics, but can also be quite helpful in time sensitive procedures such as in a trauma setting or emergency situation.

FIG. 4 is an exploded view of rotatable ring 14 of anchor device 10 depicting a ratchet mechanism. In the illustrated embodiment, rotatable outer ring 30 and bearing members 34a, b are shown separated from base 32. Multiple pin members 64a-d (more clearly shown in FIG. 6) are configured and arranged to be positioned in bearing members 34a, b to secure bearing members 34a, b to rotatable outer ring 30.

In the embodiment illustrated in FIG. 4, the disposition of sutures 20 and 21 relative to suture storage channel 40 prior to deployment is depicted. Particularly, sutures 20 and 21 are looped such that they are positioned inside suture storage channel 40. As a result, when the practitioner secures the anchor device 10 to the patient, the practitioner does not need to manage the positioning of sutures 20 and 21. Suture storage channel 40 in combination with a suture retention assembly 200 also maintains the particular desired loop formation of sutures 20 and 21 ensuring proper operation and/or deployment of sutures 20 and 21. The example suture retention assembly 200 helps maintain the sutures in position within the suture storage channel 40 during storage by covering at least a portion of the suture storage channel 40 to thereby reduce the likelihood of the sutures 20 and 21 leaving the suture storage channel 40 before the sutures 20 and 21 are deployed.

In general, this example of the suture retention assembly 200 includes a retention element and a bias element. The retention element is an example of a structural implementation of a means for retaining the sutures within the suture storage channel 40. According to one example, the retention element comprises structure for covering at least a portion of the suture storage channel 40 to retain the sutures 20 and 21 within the suture storage channel 40. According to one example, the bias element is an example of a structural implementation of a means for biasing the retention element into a position where the retention element retains the sutures 20 and 21 within the suture channel 40. In one embodiment, the bias element comprises structure for helping maintain the retention element in contact with the suture channel 40, such that the retention element covers at least a portion of the suture channel. Further, the bias element may further serve to urge the rotatable outer ring 14 away from the base 32. Particular examples of a retention element and a bias element will now be discussed in more detail.

In the example illustrated in FIG. 4, the retention element is a flat washer 202 and the bias element is a wave spring 204. The flat washer 202 and the wave spring 204 are positioned between the rotatable ring 30 and the suture storage channel 40. As will be discussed in more detail, in this example the wave spring 204 retains the sutures 20 and 21 within the suture storage channel 40 by covering at least a portion of the suture storage channel 40. In particular, the flat washer 202 is placed between wave spring 204 and the suture storage channel 40, while the wave spring 204 is placed between the flat washer 202 and the rotatable outer ring 30. The flat washer 202 may be sized such that a portion of the flat washer 202 is configured to rest on an inner lip of the suture storage channel 40. The flat washer 202 is further sized to cover a sufficient portion of the suture storage channel such that the sutures 20 and 21 are retained within the suture storage channel 40 until the sutures 20 and 21 are deployed. The inner lip of the suture storage channel may be relatively wide or flat to thereby provide a relatively flat surface on which the flat washer 202 sits to thereby increase contact between the flat washer 202 and the suture storage channel 40. Increasing the contact between the flat washer 202 and the suture storage channel 40 facilitates retention of the sutures 20 and 21 in the suture storage channel 40 to help ensure that the sutures 20 and 21 will remain in the particular desired loop formations.

With continuing reference to FIG. 4, the wave spring 204 provides a resilient biasing force against the flat washer 202 to help further ensure the flat washer 202 remains in contact with the suture storage channel 40. In particular, as previously discussed, the wave spring 204 and the flat washer 202 may be positioned between the suture storage channel 40 and the rotatable ring 30. When the flat washer 202 and wave spring 204 are thus positioned, and the rotatable ring 30 is coupled to the base 32, the wave spring 204 will be compressed. The compression causes the wave spring 204 to exert a biasing force on the flat washer 202, as previously discussed. The biasing force may help maintain the flat washer 202 in contact with the suture storage channel 40 and thereby help ensure the sutures 20 and 21 will remain in the particular desired loop formations. Retaining the sutures 20 and 21 in the desired loop formations may help ensure proper operation and/or deployment.

In addition, such a configuration may reduce the friction of the rotatable outer ring 30 relative to base 32 and the suture storage channel 40 in particular. For example, the rotatable outer ring 30, the wave spring 204, the flat washer 202 and/or the suture storage channel 40 may each be formed of materials with low coefficients of friction, such as plastic materials. As a result, the frictional forces between one or more of these components as the rotatable outer ring 30 rotates relative the base 32 may be relatively low. Further, bearing members 34a, b likewise facilitate rotation of the rotatable outer ring 30.

Specifically, with continued reference to the example illustrated in FIG. 4, the bearing members 34a, b are configured to be positioned between rotatable outer ring 30 and base 32. Bearing members 34a, b contact base 32 beneath ratchet ring 36 such that bearing members 34a, b do not contact the teeth of ratchet ring 36. Similarly, bearing members 34a, b contact rotatable outer ring 30 beneath rotatable ratchet members 38a, b such that bearing members 34a, b do not contact the teeth of rotatable ratchet members 38a, b. As a result, bearing members 34a, b do not interfere with the cooperative engagement between ratchet members 38a, b and ratchet ring 36.

A lip on each of bearing members 34a, b extends inwardly beneath ratchet ring 36. When rotatable outer ring 30 is secured to bearing members 34a, b, the lateral positioning of bearing members 34a, b secures both bearing members 34a, b and rotatable outer ring 30 to base 32. Additionally, the positioning of bearing members 34a, b maintains ratchet members 38a, b in cooperative engagement with ratchet ring 36. In the illustrated embodiment, bearing members 34a, b include a securement member for securing the suture 21 during rotation of bearing members 34a, b.

As will be appreciated by those skilled in the art, a variety of types and configurations of bearing members can be utilized without departing from the scope and spirit of the present invention. For example, in one embodiment a circular bearing member is utilized in place of two bearing member segments. In another embodiment, one or more bearing members are integrally coupled to the rotatable outer ring. In yet another embodiment one or more bearing members are integrally coupled to the ratchet members. In another embodiment, the bearing members are positioned above the ratchet ring. In yet another embodiment, a liquid bearing mechanism is utilized. In another embodiment, a roller bearing mechanism is utilized.

In the embodiment illustrated in FIG. 4, first suture channels 52a, b are positioned through base 32 and exit at extension saddle 44. First suture 20 is configured to be positioned through first suture channels 52a, b such that the ends of first suture 20a, b extend from extension saddle 44. The extension of the ends of first suture 20a, b from the extension saddle 44 allows a user to grasp the ends of first suture 20a, b to actuate first suture 20.

Second suture channels 54a, b and third suture channels 56a, b are positioned through ratchet ring 36 and base 32. Bearing member suture channels 58a, b and 60a, b are positioned through bearing members 34a, b. The second suture 21 is looped to form the first and second portions 22, 24 that intersect at loop portion 21a. The loop portion 21a of the second suture is secured to the exterior of bearing member 34a. Next, the first and second portions 22, 24 of the second suture 21 are passed through bearing member 34a, then through the ratchet ring 36 and base 32. Next, the first and second portions 22, 24 have loops with knots formed therein, as discussed in more detail with reference to FIGS. 7A and 7B. Once the loops and knots have been formed in the first and second portions 22, 24 of second suture 21, the first and second portions 22, 24 are passed through bearing member 34b. In particular, a first end 22a of first portion 22 is threaded first through bearing member channel 60a in bearing member 34a and through third suture channel 56a in ratchet ring 36 and base 32. The first end 22a of first portion 22 is then looped as desired and passed through second suture channel 54a in ratchet ring 36 and base 32. The first end 22a is then passed through bearing member channel 58a. A first end 24a of the second portion 24 is threaded first through bearing member channel 60b in bearing member 34b and through third suture channel 56b. The first end 24a of second portion 24 is then looped as desired and then passed through second suture channel 54b in ratchet ring 36 and base 32. Finally, the first end 24a of second portion 24 is threaded through bearing member channel 58b. The first ends 22a, 24a of the first and second portions 22, 24 of the second suture are then secured to the exterior of bearing member 34b.

Base 32 and ratchet ring 36 are stationary relative to the rotatable outer ring 30. As a result, second suture channels 54a, b and third suture channels 56a, b remain stationary during operation of rotatable ring 14. Bearing members 34a, b rotate in connection with rotatable outer ring 30. As a result, bearing member suture channels 58a, b and 60a, b rotate in connection with rotation of rotatable outer ring 30 and bearing member 34a, b.

When bearing members 34a, b rotate in a clockwise direction, the ends of second suture 21 are drawn around the outside diameter of base 32 beneath ratchet ring 36. As a result, the length of first suture 21 inside suture storage channel 40 is shortened. As the length of second sutures 21 inside suture storage channel 40 is shortened, the loops of suture 21 become smaller such that they can no longer fit in suture storage channel 40. This causes the suture 21 to be drawn over the inner lip of the suture storage channel 40. As the suture 21 is drawn over the inner lip of the suture storage channel 40, the suture 21 overcomes the biasing force the wave spring 204 applies to the flat washer 202. This results in automatic deployment of the loops from suture storage channel 40.

With continued reference to FIG. 4, rotatable ratchet members 38a, b engage the teeth of ratchet ring 36 to minimize counter clock-wise movement of rotatable ring 14 that would result in loosening of the suture 21. In one example, during rotation of rotatable outer ring 30, bearing members 34a, b and rotatable ratchet members 38a, b are rotated in a clockwise direction about base 32 and ratchet ring 36 in particular. Rotatable ratchet members 38a, b engage the teeth of ratchet ring 36 as rotatable ratchet members 38a, b are advanced in the clock-wise direction. When a user discontinues rotation of rotatable outer ring 30, rotatable ratchet members 38a, b engage the teeth of ratchet ring 36 minimizing movement of rotatable outer ring 30 in a counter clock-wise direction that would otherwise loosen second suture 21.

Rotatable ratchet member 38a is positioned between bearing member 34a and rotatable outer ring 30. A pivot pin is positioned on the bottom surface of each of the rotatable ratchet members 38a, b. The pivot pins are positioned in rotation bores of the corresponding bearing members 34a, b to pivotally couple rotatable ratchet member 38a to bearing member 34a. In one example, rotatable outer ring 30 contacts the upper surface of rotatable ratchet member 38a to maintain contact between the pivot pins and the rotation bores.

The end of rotatable ratchet members 38a, b, positioned opposite the pivot point provided by the pivot pin of rotatable ratchet member 38a, b and the bore of bearing members 34a, b, includes a spring member and a plurality of teeth. The plurality of teeth engage the teeth of ratchet ring 36 to minimize movement of rotatable outer ring 30 and bearing members 34a, b in a counter clock-wise direction. This spring is provided by the cutaway portion in the head of rotatable ratchet members 38a, b and the resilient nature from the material from which the heads of rotatable ratchet members 38a, b are constructed.

The suture retention assembly 200 may also help position the bearing members 34a, b relative to the base 32. As previously discussed, the flat washer 202 and the wave spring 204 are located between the suture storage channel 40 and the rotatable outer ring 30. The sutures storage channel 40 may be connected to or be part of the base 32. Further, when the rotatable outer ring 30 is coupled to the base 32, the wave spring 204 is compressed. In addition to exerting a force on the flat washer 202, the wave spring 204 also exerts a force against the rotatable outer ring 30. With reference to the example illustrated in FIG. 4, this force urges the rotatable outer ring 30 away from the base 32.

The lip on each of the bearing members 34a, b extends beneath the ratchet ring 36. The lip prevents the bearing members 34a, b and rotatable outer ring 30 from disengaging from the base 32. In particular, the lip engages the ratchet ring 36 as the rotatable outer ring 30 and bearing members 34a, b are urged away from the base 32 by the wave spring 204

Accordingly, the suture retention assembly 200 helps maintain the position of the sutures 20 and 21 within the suture storage channel 40. By maintaining the position of first suture 20 and second suture 21, disruption of the sutures before deployment of the sutures is minimized, and reliable and proper operating of anchor device 10 is maintained. As a result, the suture retention assembly 200 provides a simple and reliable mechanism for storing first suture 20 and second suture 21 beneath rotatable ring 14 during storage of anchor device 10 until such time as the sutures 20 and 21 are required to be retracted from the suture storage channel 40.

Figure 5A:
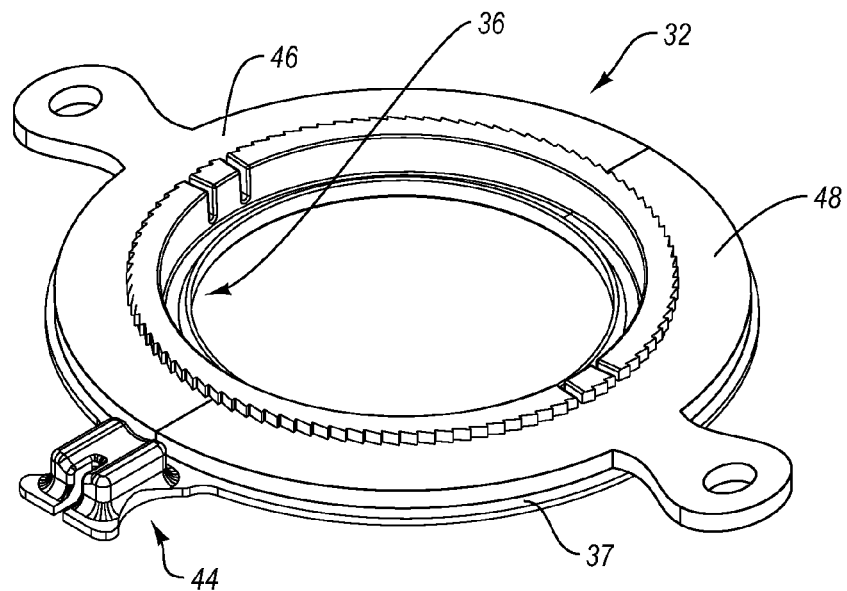
FIGS. 5A and 5B are perspective views of the base of the catheter anchor device illustrating molding of a base utilizing first and second mold members according to one example.
Figure 5B:
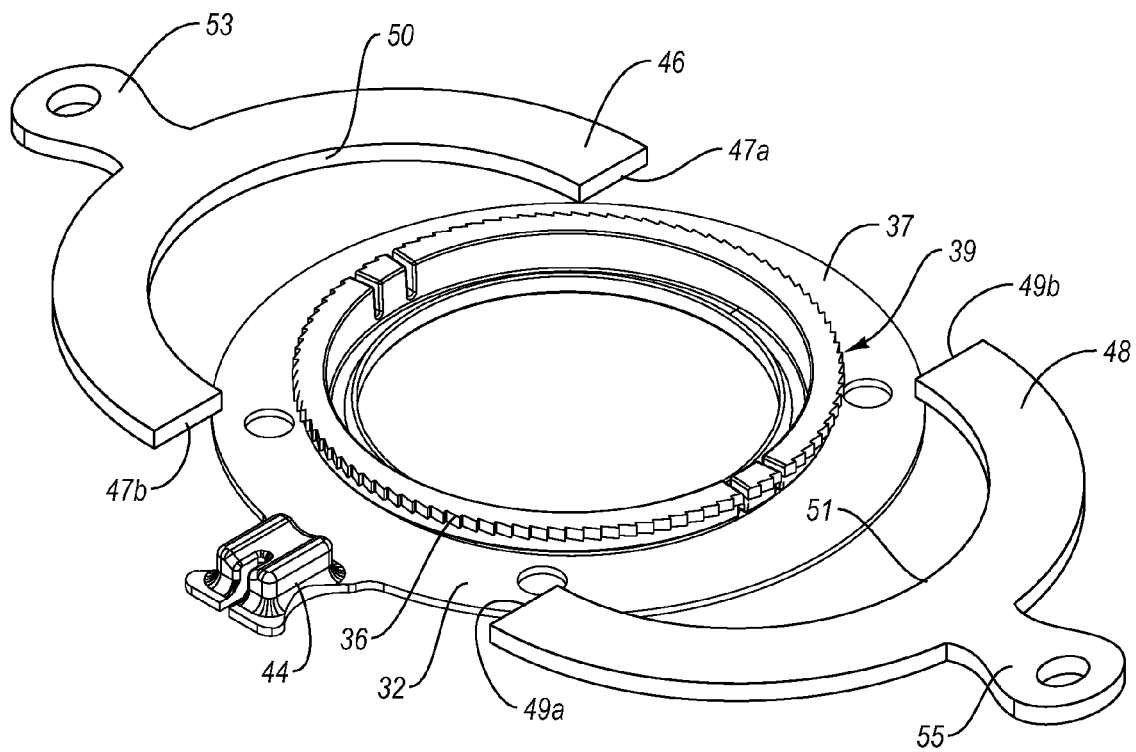

FIGS. 5A and 5B are perspective views of base 32 during molding of base 32. In the illustrated embodiment, base 32 comprises a single molded member formed utilizing first and second mold members 46 and 48. Base 32 comprises a ratchet ring 36 and an extension saddle 44. In the illustrated embodiment, base 32 includes an undercut 39 positioned between ratchet ring 36 and base flange 37. Undercut 39 substantially complicates the molding of base 32. As a result, first mold member 46 and second mold member 48 are utilized to provide the undercut 39 during the molding of base 32. For the sake of clarity, the other mold members utilized to form base 32 have not been illustrated to more clearly depict operation of first mold member 46 and second mold member 48.

In the illustrated embodiment, first mold member 46 comprises mold member interfaces 47a, b, an inner circumference 50, and a gripping handle 53. Second mold member 48 comprises mold member interfaces 49a, b, an inner circumference 51, and gripping handle 55. During molding, mold member interfaces 47a, b of first mold member 46 contact mold member interfaces 49a, b of second mold member 48. Inner circumference 50 of first mold member 46 and inner circumference 51 of second mold member 48 form the undercut 39 positioned between ratchet ring 36 and base flange 37. Inner circumference 50 and inner circumference 51 define the inner boundary of undercut 39. The top portion of first mold member 46 and second mold member 48 define the upper lateral surface extending from the innermost horizontal surface of undercut 39 (not shown) to the edge of ratchet ring 36. The bottom of first mold member 46 and second mold member 48 form the lower horizontal surface which extends from the inner vertical surface of undercut 39 (not shown) and extends outwardly to be coextensive with base flange 37.

In one embodiment, the surfaces of undercut 39 are slightly flared or tapered to allow for proper releasing of first mold member 46 and second mold member 48 such that when gripping handles 53 and gripping handle 55 are used to pull the first mold member 46 and second mold member 48 apart, first mold member and second mold member 46, 48, automatically release and can easily be slid from undercut 39. In this manner, base 32 can be molded in single member ensuring continuity of surfaces and reliable and proper operation of the components of base 32 during use of anchor device 10.

As will be appreciated by those skilled in the art, a variety of types and configurations of mechanisms can be utilized to mold base 32 in a unitary fashion without departing from the scope and spirit of the present invention. For example, first and second mold members which are configured to be automatically retracted by an automated molding apparatus or other machinery can be utilized. In another embodiment, a single mold member which is hinged, bendable, meltable or otherwise manipulable to remove the mold member from undercut 39 is utilized. In another embodiment, mold members having different form, size, and/or surfaces can be utilized. In another embodiment, more than two mold members are utilized to form the undercut and/or other portions of the base during molding.

Figure 6:
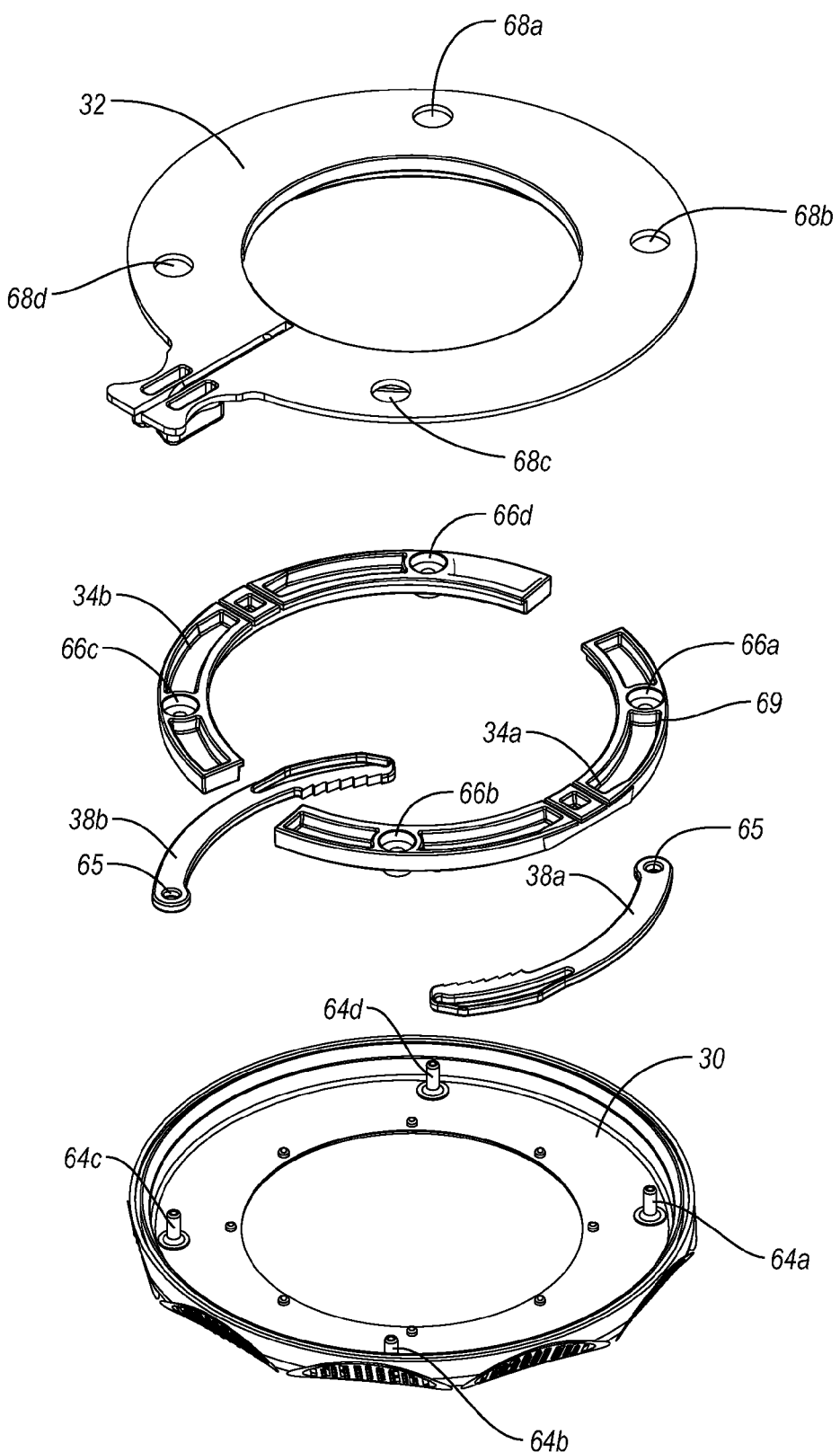
FIG. 6 is an exploded view of the catheter anchor device illustrating components of the catheter anchor device that facilitate assembly of the catheter anchor device according to one example.

FIG. 6 is a bottom exploded view illustrating the manner in which the components of anchor device 10 are secured during assembly. In the illustrated embodiment, rotatable outer ring 30, rotatable ratchet member 38a, bearing member 34a, and base 32 are depicted. Bearing members 34a, b are configured to be sandwiched between rotatable outer ring 30 and base 32. Rotatable ratchet members 38a, b are configured to be positioned between bearing members 34a, b and rotatable outer ring 30. Bearing members 34a, b are configured to be attached directly to rotatable outer ring 30 while being slidable relative to base 32. Pins 64a-d are positioned on the underside of rotatable outer ring 30 engage securement bores 66a-d of bearing members 34a, b. Bearing members 34a, b and base 32 maintain contact between securement bores 66a-d and pins 64a-d. In the illustrated embodiment, pins 64a, b are configured to be snapped to or otherwise pressed or swaged into engagement with securement bores 66a, b to couple bearing member 34a to rotatable outer ring 30 subsequent to assembly of rotatable outer ring 30 and base 32. Pins 64c, d are configured to be snapped or otherwise secured to securement bores 66c, d to integrally couple bearing member 34b to rotatable outer ring 30 subsequent to assembly of rotatable outer ring 30 and base 32. In one example, the pins are formed with enlarged heads. The enlarged heads provide a rivet function in that when pressed through bearing members 34a, b, the heads lock the rotatable outer ring to the bearing members 34a, b. In addition, ultrasound or thermal deformation may be used to lock the pins 64c, d into the base 32. A plurality of access bores 68a-d are provided in connection with base 32 such that the welding tool can be inserted through access bores 68a-d to weld pins 64a-d to securement bores 66a-d of bearing members 34a, b.

Rotatable ratchet members 38a, b are positioned, respectively, between bearing members 34a, b and rotatable outer ring 30. In the illustrated embodiment, the pivot pins 69 are positioned on the upper surface of bearing members 34a, b. The pivot pin 69 is positioned in rotation bores 65 to pivotally couple rotatable ratchet members 38a, b to bearing members 34a, b. Rotatable outer ring 30 contacts the upper surface of rotatable ratchet members 38a, b to maintain contact between the pivot pins 69 and rotation bores 65. Additionally, the outer horizontal portion of the rotatable outer ring 30, which extends downward adjacent rotatable ratchet members 38a, b, allows lateral movement of the free end of rotatable ratchet members 38a, b to ensure proper operation and contact between the teeth of rotatable ratchet members 38a, b and the teeth of ratchet ring 36 (illustrated in FIGS. 5A and 5B). In one example, the components discussed above may be positioned relative to each other and then snapped into place. Such a configuration may increase the manufacturability of the anchor device 10.

As will be appreciated by those skilled in the art, a variety of types and configurations of mechanisms for securing the components of the rotatable ring can be utilized without departing from the scope and spirit of the present invention. For example, in one embodiment, the bearing member is configured to be snapped to the rotatable outer ring before assembly with the base. In another embodiment, a snap fitting is provided between the bearing member and the rotatable outer ring. In another embodiment, a continuous bearing member is integrated with the base 32 while the rotatable ratchet member is secured independently to the rotatable outer ring. In yet another embodiment, a surface is provided on the bearing member to maintain proper operation of the rotatable ratchet member.

Figure 7A:
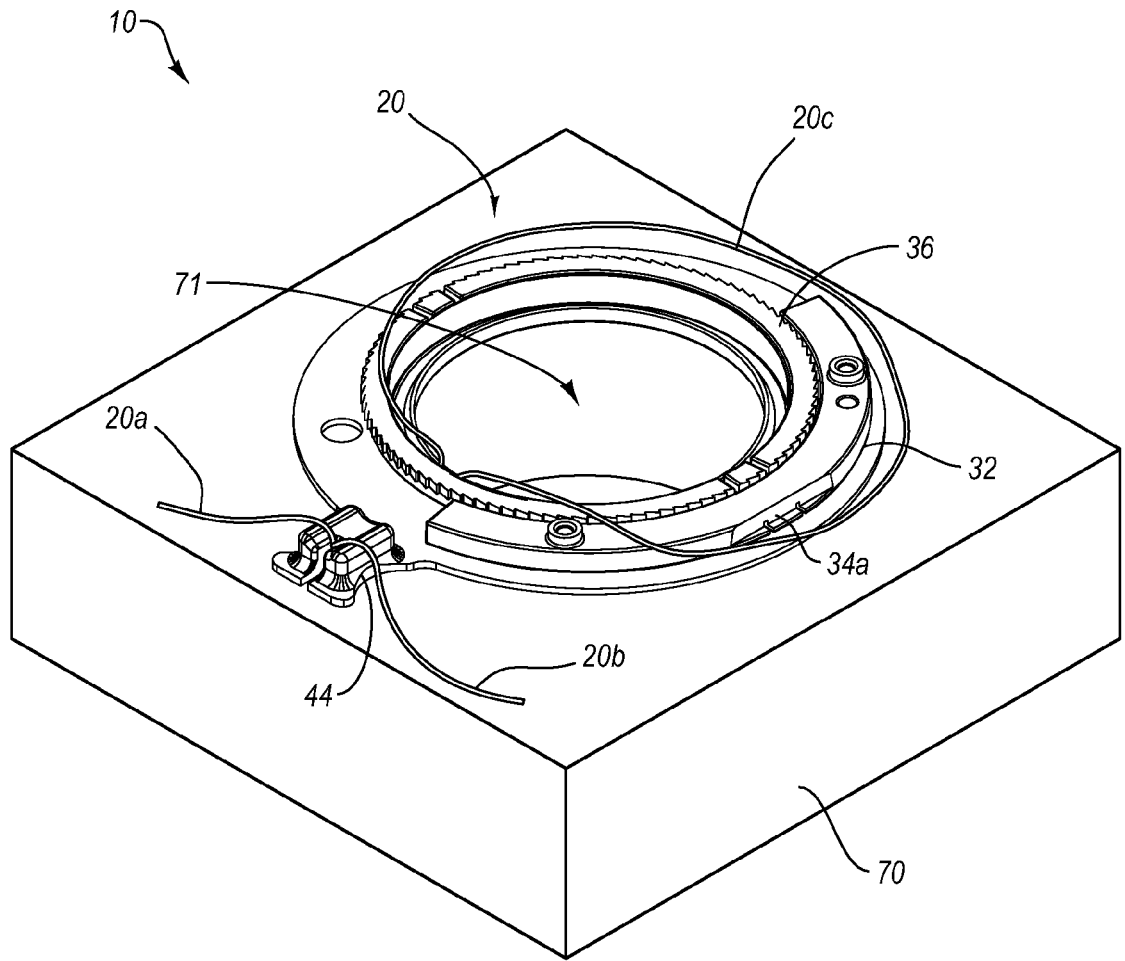
FIGS. 7A and 7B are perspective views of the base of the catheter anchor device, illustrating loading of the sutures and a suture retention assembly during assembly of the catheter anchor device according to one example.
Figure 7B:
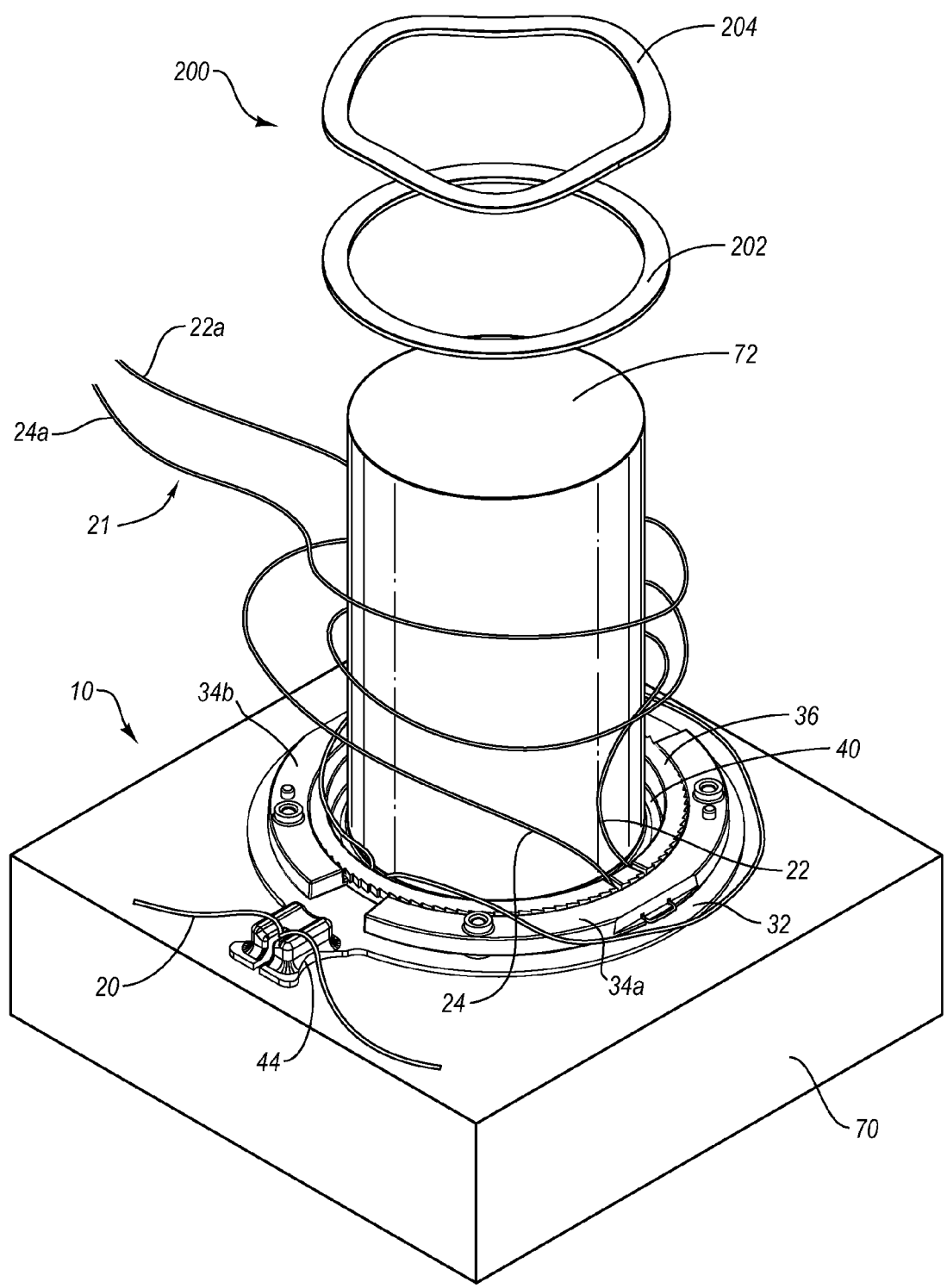

FIGS. 7A and 7B illustrate loading of the sutures utilized with anchor device, according to one embodiment of the present invention. In particular, as seen in FIG. 7A, base 32 of anchor device 10 is mounted on a loading block 70. The anchor device 10 is positioned over the center bore 71 of loading block 70. First suture 20 is partially loaded into the base 32. More specifically, the ends 20a, b of first suture 20 are threaded from the interior of the ratchet ring 36 through the base 32 to extend beyond the extension saddle 44. The loop portion 20c of first suture 20 is looped about the perimeter of the base 32. The ends 20a, b of the first suture 20 may be threaded through the extension saddle 44 either before or after the base 32 is mounted to a loading block 70. Thereafter, the second suture 21 may be loaded.

As illustrated in FIG. 7B, a suture loading cylinder 72 is positioned through center bore 71 (FIG. 7A) such that the wall of the suture loading cylinder 72 is positioned adjacent the inner portion of ratchet ring 36. Suture loading cylinder 72 is utilized to provide a quick and effective mechanism for forming the loop configurations of first suture 20 and second suture 21 and for loading the sutures 20, 21 in base 32.

In the illustrated embodiment, the loops of second suture 21 are being formed around suture loading cylinder 72. First suture 20 has previously been located about the perimeter of base 32. Initially, the second suture 21 is doubled over to form the first and second portions 22, 24 that are connected by a loop portion 21a. More particularly, as illustrated in FIG. 4, the first end 22a of first portion 22 is threaded first through bearing member channel 60a in bearing member 34a and through third suture channel 56a in the ratchet ring 36 and base 32. A first end 24a of the second portion 24 is threaded first through bearing member channel 60b in bearing member 34a and through third suture channel 56b in the ratchet ring 36 and base 32. Returning to FIG. 7B, after the first ends 22a, 24a, of the first and second portions 22, 24 of the second suture 21 have been threaded through the ratchet ring 36 and base 32, loops are formed in the first second portions 22, 24. One loop is substantially formed by wrapping the length of first portion 22 about suture loading cylinder 72 in a manner so as to produce the desired loop configuration in the first portion 22 of the second suture 21. The second portion 24 is also wrapped to form the desired loop configuration. Once the loops have been formed in the first and second portion 22, 24, the ends 22a, 24a of the second suture 21 are threaded through the ratchet ring 36 and base 32 and then the bearing member 34b and secured.

As the loops of first and second portions 22, 24 are drawn tight and the loop portion 21a is secured relative to bearing members 34a and base 32, the loops of the first and second portions 22, 24 of the second suture 21 are automatically drawn down such that both the first and second portions 22, 24 are loaded within ratchet ring 36 in the desired position for deployment. Once second suture 21 has been loaded into the base 32, additional loops or knots may be formed in the first suture 20 using the suture loading cylinder 72. The first suture 20 may then be drawn tight such that the first suture 20 is drawn into the suture storage channel 40. As will be appreciated by those skilled in the art, similar steps, acts, and processes are utilized to load first suture 20 and second portion 24. The discussion of the formation of loops in the second suture and the loading of second suture 21 in base 32 is for illustrative purposes and should in no way be considered to be limiting in nature.

Once first suture 20 and second suture 21 have been properly loaded in storage channel 40, the flat washer 202 is positioned over the top of suture loading cylinder 72. The flat washer 202 is lowered along the length of suture loading cylinder 72 until the flat washer 202 is positioned along the inner circumference of ratchet ring 36, effectively maintaining the position of first suture 20 and second suture 21 in their desired position within storage channel 40. Next, the wave spring 204 is lowered along the length of the suture loading cylinder 72 until the wave spring 204 is positioned on the flat washer 202. Once the flat washer 202 and wave spring 204 have been properly positioned within base 32, suture loading cylinder 72 is withdrawn and rotatable outer ring 30 is lowered into engagement with base 32 as discussed with respect to FIG. 6. The proper steps can then be taken to couple rotatable outer ring 30 to bearing members 34a, b as discussed with respect to FIG. 6.

As will be appreciated by those skilled in the art, a variety of types and configurations of mechanisms for loading the sutures in the suture storage channel can be utilized without departing from the scope and the spirit of the present invention. For example, in one embodiment, a loading block and suture loading cylinder are utilized to manually load the sutures in the anchor device. In another embodiment, the loading block and suture loading cylinder are utilized with automated processes to load the sutures into the base or other component of the anchor device.

Figure 8A:
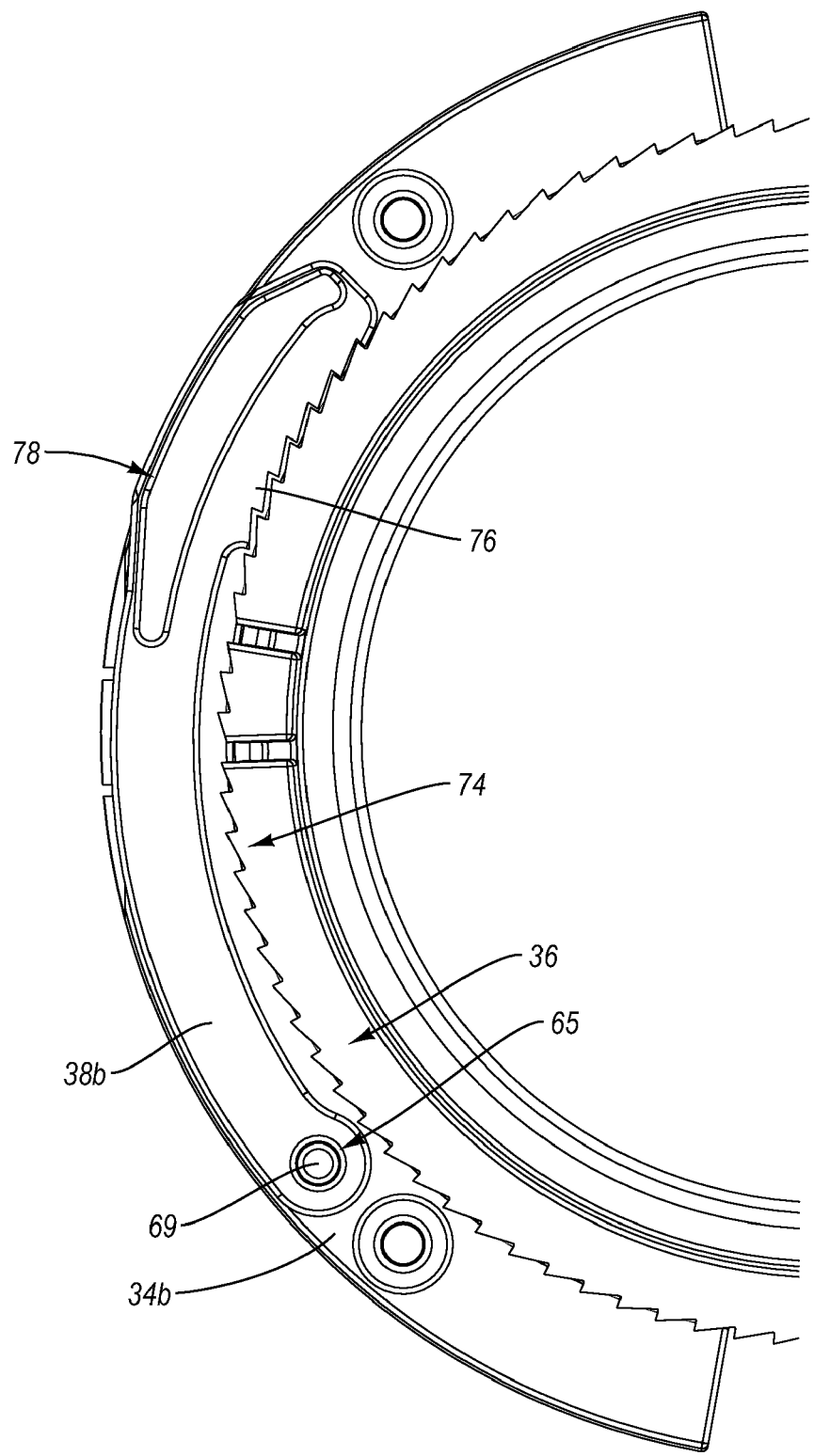
FIGS. 8A and 8B are component views illustrating the ratchet mechanism including operation of a rotatable ratchet member relative to the ratchet ring according to one example.
Figure 8B:
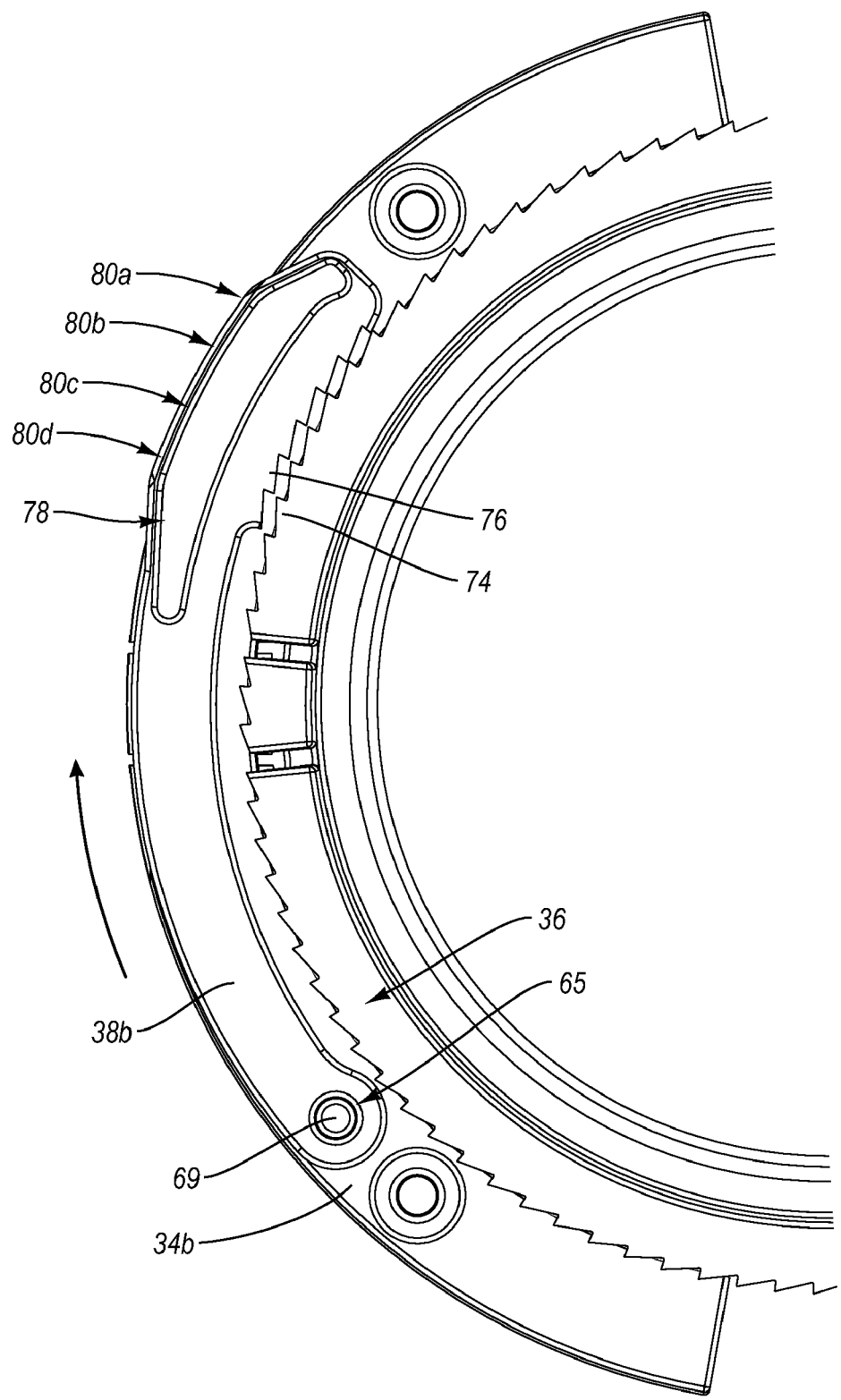

FIGS. 8A and 8B illustrate rotatable ratchet member 38b in operation with respect to ratchet ring 36. While rotatable ratchet member 38b is shown for illustrative purposes, it will be understood by those skilled in the art that operation of rotatable ratchet member 38b also is exemplary of rotatable ratchet member 38a (see FIG. 4.) In the illustrated embodiment, rotatable ratchet member 38b is rotatably coupled to bearing member 34b utilizing pivot pin 69 and rotation bore 65 of rotatable ratchet member 38b. Rotatable ratchet member 38b engages the teeth of ratchet ring 36 to minimize counterclockwise movement of rotatable ring 14 that would result in loosening of the second suture 21 (not shown). Rotatable ratchet member 38b is secured to bearing member 34b by pivot pin 69 located between the upper surface of bearing member 34b and the bottom surface of rotatable outer ring 30 (see FIG. 4). Pivot pin 69 is positioned in the rotation bore 65 of rotatable ratchet member 38b such that rotatable ratchet member 38b can pivot about pivot pin 69.

The rotatable ratchet member 38b is held in place relative to bearing member 34b by being sandwiched between bearing member 34b and rotatable outer ring 30 (see FIG. 4). Thus, during rotation of rotatable outer ring 30 (see FIG. 4), bearing member 34b and rotatable ratchet member 38b are rotated in a clock-wise direction about ratchet ring 36. Rotatable ratchet member 38b engages the teeth of ratchet ring 36 as rotatable ratchet member 38b is advanced in the clock-wise direction. When a user discontinues rotation of the rotatable outer ring 30, rotatable ratchet member 38b engages the teeth of ratchet ring 36 minimizing movement of rotatable outer ring 30 in a counter clock-wise direction that would otherwise loosen the sutures.

The end of rotatable ratchet member 38b positioned opposite the rotation bore 65 and pivot pin 69 includes a ratchet member engagement spring 78 and rotatable ratchet member teeth 76. Rotatable ratchet member teeth 76 engage the ratchet ring teeth 74 to minimize movement of the rotatable outer ring 30 and bearing member 34b in a counter clock-wise direction. Ratchet member engagement spring 78 is provided by the cutaway portion in the head of rotatable ratchet member 38b. The nature of the material from which the head of rotatable ratchet member 38b is constructed provides sufficient resilience to undergo deformation while maintaining contact between rotatable ratchet member teeth 76 and ratchet ring teeth 74.

As the rotatable ratchet member teeth 76 slide over ratchet ring teeth 74, ratchet member engagement spring 78 flexes slightly to maintain contact between rotatable ratchet member teeth 76 and ratchet ring teeth 74. This is caused by the ramp-like configuration of rotatable ratchet member teeth 76 and ratchet ring teeth 74. When the rotatable ratchet member teeth 76 pass over the outer most ridge of ratchet ring teeth 74 such that they engage new teeth, ratchet member engagement spring 78 forces the rotatable ratchet member teeth 76 toward the center of the anchor device 10, thus maintaining engagement with ratchet ring teeth 74. As previously introduced, according to one embodiment, the rotatable ratchet members 38a, b may be integral with the bearing members 34a, b.

Figure 9A:
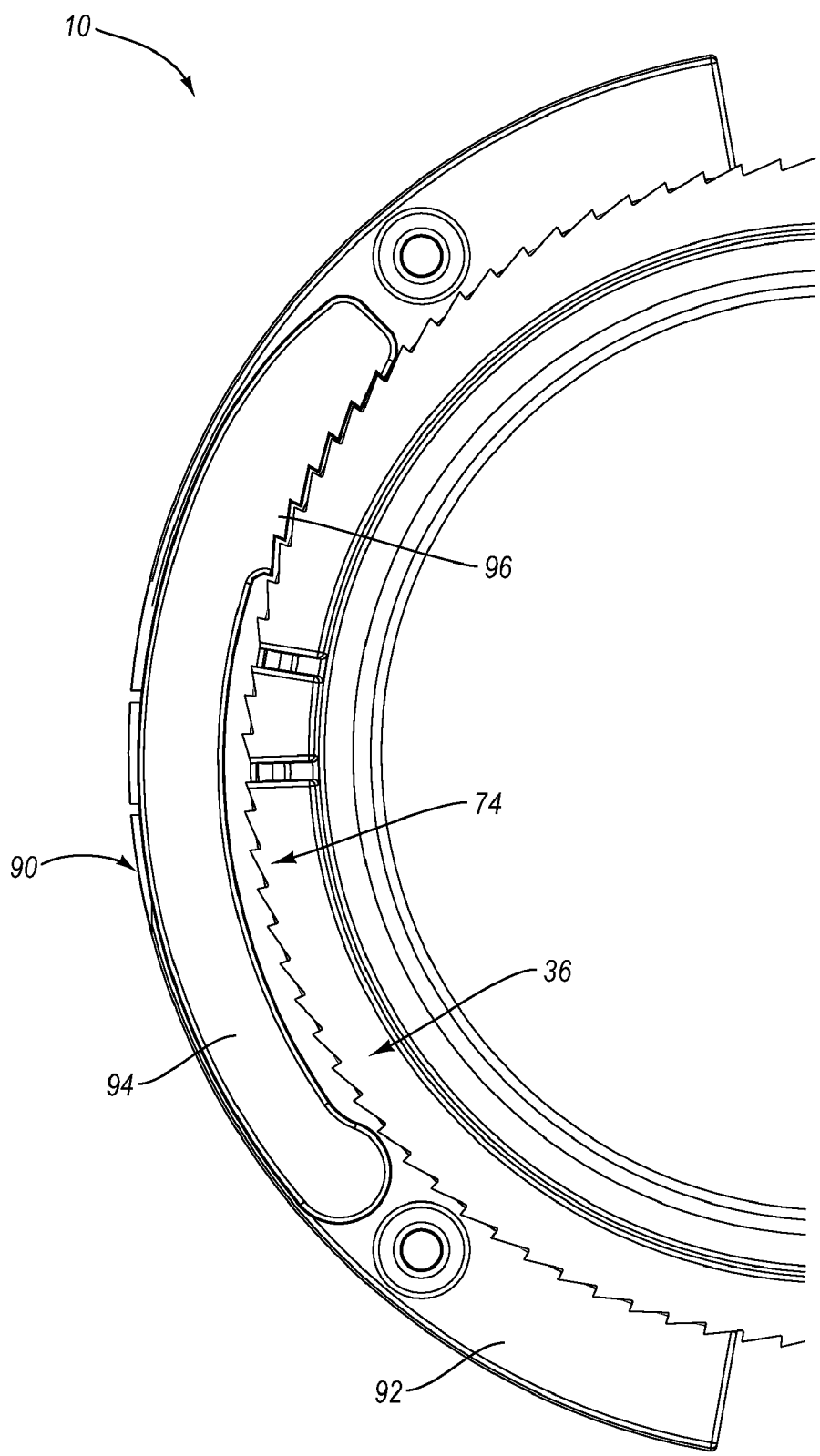
FIGS. 9A and 9B are component views illustrating a ratchet mechanism that includes an integral ratchet and bearing member, including operation of a rotatable ratchet member relative to the ratchet ring according to one example.
Figure 9B:
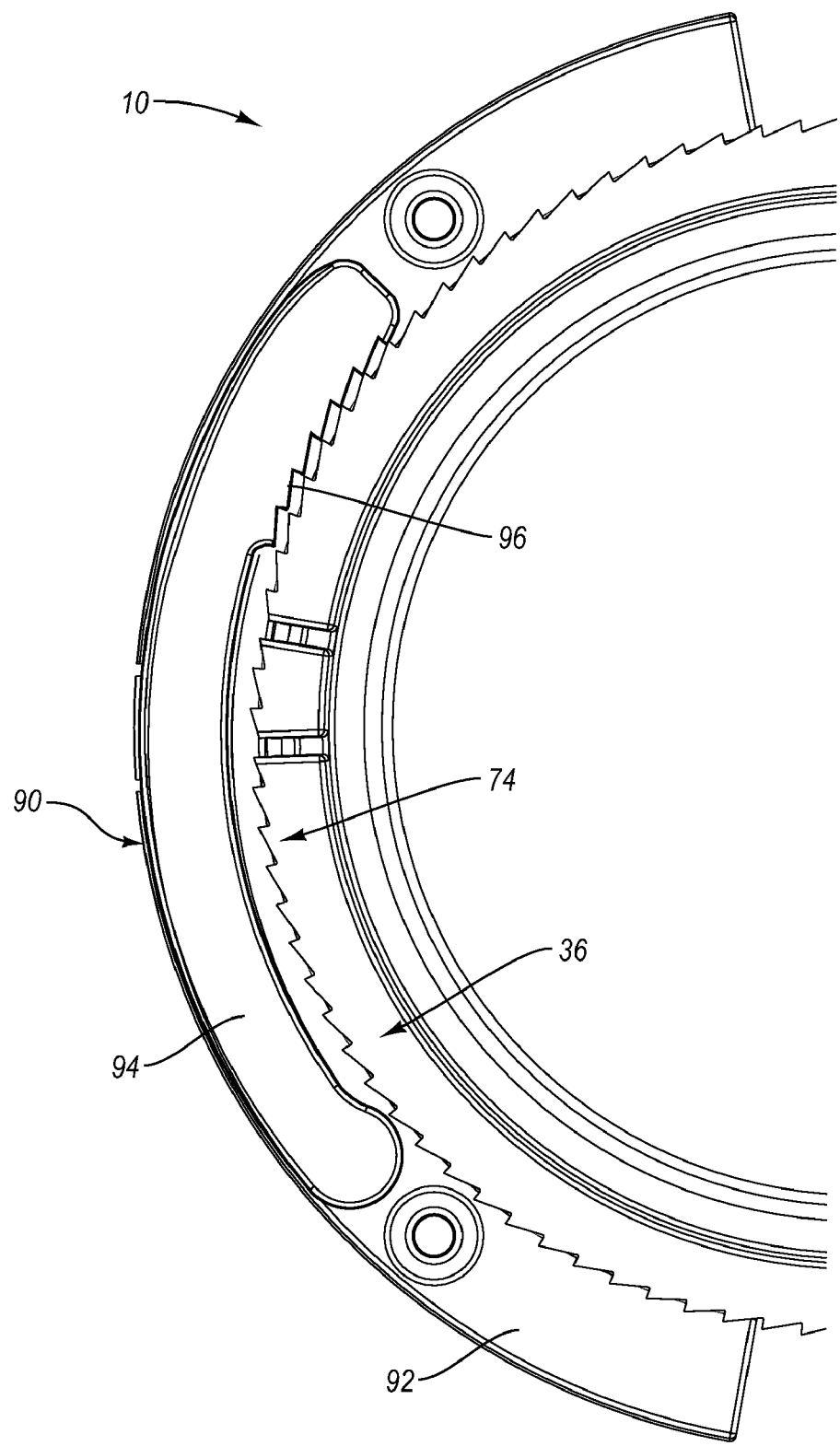

FIGS. 9A and 9B illustrate an integral ratchet and bearing member 90 engaged with a ratchet ring 36. As illustrated in Figured 9A, the integral ratchet and bearing member 90 includes a bearing member portion 92 and a ratchet portion 94. In one embodiment, the ratchet portion 94 is integrally formed with the bearing member 92, such that the bearing member portion 92 and the ratchet portion 94 are a single piece. The ratchet portion 94 includes ratchet teeth 96. Ratchet teeth 96 engage the ratchet ring teeth 74 to minimize movement of the ratchet and bearing member 90 in a counter clock-wise direction. The material from which the ratchet portion 94 is constructed provides sufficient resilience to undergo deflection while maintaining contact between ratchet teeth 96 and ratchet ring teeth 74.

For example, in the configuration illustrated in FIG. 9A, the ratchet portion 94 is partially deflected. In particular, in the absence of contact with the ratchet ring 36, the portion of the ratchet portion 94 that includes ratchet teeth 96 would be closer to the center of the anchor device 10. Positioning the ratchet portion 94 relative to the ratchet ring 36 results in the partial deflection of the ratchet portion 94. The partial deflection of the ratchet portion 94 provides a biasing force that helps maintain the contact between ratchet teeth 96 and ratchet ring teeth 74 as shown in FIG. 9A. The ratchet portion 94 is also configured to be further deflected, as illustrated in FIG. 9B.

As the ratchet teeth 96 slide over ratchet ring teeth 74, the ratchet portion 94 is further deflected. As the ratchet portion 94 is further deflected, the tendency of the ratchet portion 94 to move toward an undeflected position helps maintain contact between rotatable ratchet teeth 96 and ratchet ring teeth 74. When the ratchet teeth 96 pass over the outermost ridge of ratchet ring teeth 74 such that the ratchet teeth 96 engage new ratchet ring teeth 74, the tendency of the ratchet portion 94 to return to an undeflected position forces the ratchet teeth 96 toward the center of the anchor device 10, thus maintaining engagement with ratchet ring teeth 74.

As will be appreciated by those skilled in the art, a variety of types and configurations of rotatable ratchet members can be utilized without departing from the scope and spirit of the present invention. For example, in one embodiment, the rotatable ratchet members prevent rotation of a rotatable ring in a clock-wise direction. In another embodiment, the rotatable ratchet members prevent backward movement of a nonrotational actuation member. In another embodiment, a secondary spring separate from the body of the rotatable ratchet member provides the spring movement of all or part of the rotatable ratchet member.

Anchor devices may be embodied in other specific forms without departing from the spirit or essential characteristics of the invention. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A catheter anchor device for use with a catheter, the anchor device comprising:
   a stationary base secured to the patient;
   a rotatable ring secured to the stationary base such that the rotatable outer ring can be rotated by the user relative to the stationary base;
   one or more sutures positioned internally within the rotatable ring such that actuation of the rotatable ring automatically deploys the one or more sutures from within the rotatable ring to engage a sidewall of the catheter and to secure the catheter relative to the rotatable ring;
   a ratchet mechanism mechanically operable with the rotatable ring such that when a user rotates the rotatable ring, the ratchet mechanism is engaged during rotation of the rotatable ring, the ratchet mechanism comprising a rotatable ratchet member which maintains cooperative engagement of the components of the ratchet mechanism allowing movement of the rotatable ring in a first direction while minimizing inadvertent movement of the rotatable ring in a second direction securing the rotational position of the rotatable ring against movement in the second direction;
   means for retaining the one or more sutures in a desired location relative to the base; and
   means for biasing, the means for biasing cooperating with the means for retaining to aid in retention of the one or more sutures in a desired location relative to the base.

2. The catheter anchor device of claim 1, wherein the rotatable ratchet member comprises a spring.

3. The catheter anchor device of claim 1, wherein the rotatable ratchet member comprises a resilient component.

4. The catheter anchor device of claim 1, wherein the rotatable ratchet member includes a pivot point at one end and one or more teeth at the opposing end.

5. The catheter anchor device of claim 4, wherein the ratchet mechanism comprises one or more stationary teeth and wherein the teeth of the rotatable ratchet member pass over the stationary teeth during movement of the rotatable ring.

6. The catheter anchor device of claim 5, wherein the rotatable ratchet member allows biasing of one or more components of the ratchet mechanism allowing the one or more teeth of the rotatable ratchet mechanism to pass over the stationary teeth while maintaining contact between the one or more teeth of the rotatable ratchet mechanism and the stationary teeth.

7. The catheter anchor device of claim 6, wherein the rotatable ratchet member comprises a pivot point which allows for movement of the one or more teeth of the rotatable ratchet mechanism allowing passage of the one or more teeth of the rotatable ratchet mechanism over the stationary teeth.

8. The catheter anchor device of claim 6, wherein a rotatable ratchet member engagement spring is positioned adjacent the one or more teeth of the rotatable ratchet mechanism to maintain contact between the one or more teeth of the rotatable ratchet mechanism and the stationary teeth.

9. The catheter anchor device of claim 8, wherein the rotatable ratchet member engagement spring comprises a resilient component of the head of the rotatable ratchet member which deforms as the teeth of the rotatable ratchet member pass over the stationary teeth.

10. The catheter anchor device of claim 1, wherein the means for biasing exerts a force on the rotatable outer ring in a direction away from the stationary base.

* * * * *